United States Patent [19]

Strelkauskas

[11] Patent Number: 4,724,211
[45] Date of Patent: Feb. 9, 1988

[54] HUMAN MONOCLONAL ANTIBODIES AND LYMPHOKINES AND CELL LINES PRODUCING SAME

[75] Inventor: Anthony J. Strelkauskas, Isle of Palms, S.C.

[73] Assignee: Medical University of South Carolina, S.C.

[21] Appl. No.: 883,441

[22] Filed: Jul. 14, 1986

Related U.S. Application Data

[60] Continuation of Ser. No. 616,495, Jun. 1, 1984, abandoned, which is a division of Ser. No. 398,839, Jul. 16, 1982, abandoned, which is a continuation-in-part of Ser. No. 328,738, Dec. 8, 1981, abandoned.

[51] Int. Cl.$^4$ .................. C12N 5/00; C12N 15/00; C12P 21/00; A61K 39/395
[52] U.S. Cl. .................. 435/240.27; 435/172.2; 435/68; 435/948; 530/387; 436/548; 935/100; 935/92; 935/101; 424/85
[58] Field of Search .................. 435/68, 172.2, 240, 435/241, 948; 436/548; 935/100, 110; 530/387

[56] References Cited

U.S. PATENT DOCUMENTS

| | | | |
|---|---|---|---|
| 4,377,513 | 3/1983 | Sugimoto et al. | 435/172.2 |
| 4,434,230 | 2/1984 | Ritts, Jr. | 435/948 |
| 4,522,918 | 6/1985 | Schlom et al. | 435/172.2 |

OTHER PUBLICATIONS

Schlom et al., "Generation of Human Monoclonal Antibodies Reactive with Human Mammary Carcinoma Cells", Proceedings of the National Academy of Sciences, 77 (11), pp. 6841–6845, (1980).
Mesa-Tejada et al., "Detection in Human Breast Carcinomas of an Antigen Immunologically Related to a Group-Specific Antigen", Proceedings of the Natonal Academy of Sciences, 75 (3), pp. 1529–1533, (1978).
Leung et al., "Frequency of Association of Mammary Tumor Glycoprotein Antigen and Other Markers with Human Breast Tumors", Cancer Research, 39, pp. 2057–2061, (1979).
Sheikh et al., "Ductular Carcinoma of the Breast: Serum Antibodies to Tumor-Associated Antigens", Cancer, 44, pp. 2083–2089, (1979).
Nowinski et al., "Human Monoclonal Antibody Against Forssman Antigen", Science, 210, pp. 537–539, (1980).
Howard et al., "A Method for distinguishing Benign from Malignant Breast Lesions Utilizing Antibody Present in Normal Human Sera", Cancer, 43, pp. 2279–2287, (1979).

*Primary Examiner*—John E. Tarcza

[57] ABSTRACT

A method is described for separating fused cells, resulting from fusion of human cells known to produce a specific antibody or a specific lymphokine with malignant human partner cells, from the said partner cells which comprises addition of specific antiserum capable of identifying antigenic specificities unique to the clone and non-reactive with the non-fused partner cells. After reaction of the fused cell with the antiserum, the reaction product is separated within 24 hours by indirect rosetting.

One cell line, ATCC HB-8143, secreted both IgG and IgM monoclonal antibodies, both antibodies having specificity to human breast carcinoma and being highly selective therefor.

2 Claims, No Drawings

HUMAN MONOCLONAL ANTIBODIES AND LYMPHOKINES AND CELL LINES PRODUCING SAME

This is a continuation of application Ser. No. 616,495, filed June 1, 1984, now abandoned which is a division of application Ser. No. 398,839, filed July 16, 1982, now abandoned, which is a continuation-in-part of application Ser. No. 328,738, filed Dec. 8, 1981, now abandoned.

The present invention relates to a new method of producing lymphokines and monoclonal antibodies of high specificity useful in diagnosis and therapy using a human-human hybridoma technique which does not require the use of enzyme deficient malignant partner cells, a specific human-human hybridoma cell line, and the monoclonal antibodies produced thereby.

More specifically the invention relates to a novel method of separating fused cells resulting from fusion of a human cell known to produce a specific antibody with a malignant human partner cell, which does not need to be enzyme deficient, from the said partner cell and subsequent culturing of the fused cells. This separation technique utilizes the reaction of the fused cell with antiserum and separation of the fusion product with the antiserum within 24 hours by indirect rosetting. A new method of subculturing is provided using multiple fractionations of putative clones limiting the number of cells per well to about 500.

Instead of the cell producing a specific antibody, there may also be used a human cell producing a specific lymphokine (immunomodulator) such as leucocyte inhibitory factor, interferon, Interleukin II, Suppressor Factor, and the like.

In practice of this invention patients are selected for their ability to produce particular lymphokines or certain antibodies. Among the antibodies are those with specificity useful in diagnosis and therapy of human disease. Among the diseases in which these human monoclonal antibodies will be useful for diagnosis are those in which there is a shedding of antigen into the peripheral system.

Useful specificities are exemplified by the carcinomas and especially clinical types of mammary carcinoma, as well as viral conditions such as herpes (e.g., Type I and II), and tetanus.

A group of disease conditions in which the anti-T cell antibodies produced by this invention are of value are immunoregulatory disorders, exemplified by autoimmune diseases and immunodeficiency states and particularly adult and juvenile rheumatoid arthritis, systemic lupus, severe combined immunodeficiency as well as hyper- and hypogammaglobulinemia.

Another field of diagnostic and therapeutic utility comprises the field of organ transplants. By use of anti-T cell antibodies, it is possible to monitor cells involved in graft rejection and to modulate the number of cells, thereby eliminating in many cases the onset and severity of graft rejection crises.

The technique of this invention can also be used to produce a hybrid clone which secretes a variety of immune modulators, lymphokines, such as the leucocyte inhibiting factor (LIF) and Interleukin II. Up to now, it has been difficult to purify such lymphokines. The availability of hybrid clones of this invention producing distinct lymphokines opens new pathways to their production and characterization.

Lymphocytes are taken from the patient producing antibodies or lymphokines of a specificity as described above, typically from the peripheral blood, and fused with a malignant human partner cell. This partner cell can be selected from cell cultures such as those available from RPMI (Rosewell Park Memorial Institute, Buffalo, NY. Preferred are cells with characteristics of rapid growth, good stability and high fusion efficiency.

As a result of fusion of the antibody producing cell with the said partner, there results a mixture of
(1) fused cells;
(2) non-fused antibody producing cells; and
(3) non-fused malignant partner cells.

For the separation of the fused cells from this mixture, the prior art has taught the need to employ an enzyme deficient fusion partner, specifically an HAT (hypoxanthine-aminopterin-thymidine) sensitive cell. The disadvantages of use of such human partners are:
(1) a decrease in the efficiency of fusion to produce hybrid clones;
(2) loss of rapid growth characteristics;
(3) increased genetic instability; and
(4) logistical difficulty associated with the selection and maintenance of enzyme deficient mutant malignant fusion partner cells which is time consuming and expensive.

The present invention avoids the need to use such enzyme deficient fusion partners. Instead, there is used the technique of positive selection of the clones from the non-fused partner by the addition of a specific antiserum which identifies antigenic specificities unique to the clone and is non-reactive with the non-fused partner cells. These antisera are available as HLA (Human leucocyte antigen) typing reagents. It will be obvious to those skilled in the art that in selecting a partner cell, one of a different HLA type must be used. Reaction of the fused cell with the antiserum is typically completed within 60 minutes.

The positive selection of the fused clone cell from the non-fused partner cell, which has not reacted with the antiserum, is carried out within 24 hours by the conventional indirect rosetting technique, using density gradient centrifugation.

There is thus separated from the nonfused malignant partners a mixture of fused clone cells and the non-fused antibody or lymphokine producing cells. These non-fused cells have a relatively short life, typically no more than 10 days while the fused clone cells survive and multiply in culture.

In sub-culturing individual clones, a technique different from that employed with murine cultures is used. While in the case of the murine culture, individual cells may be set into subculture and made to grow, this technique has not been found effective with human clones. It has been found useful to proceed by multiple fractionations of putative clones, so that the limiting number of cells per well during subculturing is approximately 100–500.

There are thus obtained cultures of clones which selectively produce specific antibodies useful in diagnosis and therapy as discussed above.

The specific antibodies are obtained from batch cultures using conventional methods such as affinity column chromatography or preparative isoelectric focusing. The isolated antibodies are used as such or are incorporated in per se known manner into pharmaceutical compositions such as solutions, test kits, or radioimmune assay materials.

In a further aspect of the present invention, there is provided a human monoclonal antibody which is useful for the identification of various malignancies, with specific testing in vitro to show the presence of human mammary cancer antigens. Tests conducted with human monoclonal antibodies designed to "recognize" the presence of human mammary cancer have been done under the microscope using conventional indirect fluoresence and shown to be useful in reacting with the human mammary cancer. In a generic embodiment for the identification of mammary cancer there is thus provided a method which comprises contacting serum or ductile secretion from the mammary region of said subject with a human monoclonal antibody, said human monoclonal antibody being derived from the fusion of a normal human blood lymphocyte producing an antibody with specificity for mammary carcinoma, and a malignant partner cell. A positive reaction between said human monoclonal antibody and said serum or ductile secretion indicates the presence in said subject of tumor antigens, suggesting the presence of mammary carcinoma cells.

In a preferred embodiment the malignant partner cell is an acute lymphocytic leukemia cell of the B or T type. The positive reaction whereby the indication of human mammary cancer is suggested may be, for example, through precipitation of the human monoclonal antibody with the serum or ductile secretion, or through indirect fluorescence.

Although T lymphocytes do not produce immunoglobulins themselves, they have been found to be highly effective fusion partners for purposes of this invention. Thus the use of B cells as malignant fusion partners is not a requirement for production of antibody secreting clones. The selection of particular malignant cell lines is not critical, provided that they are vigorous and of long life. The special advantage of the use of T cells is the availability of more stable hybrids which are relatively resistant to genetic change and long lived.

The invention also has special utility in the field of juvenile rheumatoid arthritis where during periods of exacerbation certain antibodies are present, which are absent during remission. Human hybridoma cells lines are provided herein using lymphocytes from patients during exacerbation with lymphoblastoid T cells, which have been found especially effective as fusion partners; the resulting clones secrete antibody which identifies a subset of normal human peripheral blood T lymphocytes similar to those identified by autoimmune antibodies found in sera of such patients. These antibodies have applicability as specific probes for examination of the T cell population and potentially for modulating specific immune response in vivo.

In one embodiment, a human hybridoma cell line, designated JDB1 and on deposit at the American Type Culture Collection, Rockville, Md., under the designation ATCC No. HB-8143 has now been shown to be a stable clone which secretes both IgG and IgM monoclonal antibodies, both antibodies having the same specificity, which bind to human breast cancer cells and are highly selective therefore.

The following examples are provided for purposes of illustrating the invention in further detail. They are not to be construed as limiting the invention in spirit or in scope. Persons skilled in the art will recognize that equivalent antigens, reagents, subjects, cells, and procedures can be adopted without departing from the scope of the invention.

EXAMPLE I

A group of patients is screened for reactivity against long term cell lines derived from mammary carcinoma tissue. Selected patients with serum reactivity against particular lines are bled and then HLA typed. The lymphocytes are separated using a polysaccharide density gradient such as Ficoll-Hypaque.

20,000,000 isolated lymphocytes are mixed with 10,000,000 malignant fusion partner cells, such as Ball-1, a cell line derived from a patient with acute lymphoma of a B cell variety in the presence of polyethylene glycol. The mixture is centrifuged at 400 g and incubated for a total of 8 minutes at which time the cells are washed and placed in culture for a period of about 20 hours.

At this time, the cells are washed and incubated with the anti-HLA reagent appropriate according to the result of the typing. After 60 minutes, the cells are washed and rosetted with human red blood cells which are coated with affinity column purified anti-IgG. The indirect rosetted mixture is carefully layered onto a Ficoll-Hypaque density gradient and centrifuged at 1400 g for 15 minutes. The non-rosetted non-fused malignant partner cells are located at the interface and are removed.

The rosetted fused and non-fused antibody producing cells are located in the pellet. These are treated with buffered ammonium chloride to remove the red cells and the cells are washed and placed in culture at a concentration of 2,000,000 cells per well in 24 well plates. The culture is maintained at 37° C. in 5% carbon dioxide atmosphere until maximum growth is observed, typically in 5–7 days. Each well is then sub-cultured so that 100–500 cells are placed into each new subculture well. These subcultured cells are allowed to grow to a concentration of approximately 100,000, after which subculturing is repeated. The specificity of the antibody being produced is advantageously ascertained after each subculturing step.

Subcultures with the appropriate specificity are then grown to large levels and supernatants are collected routinely. The antibody is isolated from these supernatant by conventional immunochemical techniques. A typical subculture producing antibody to one form of mammary carcinoma as evidenced by reactivities to the mammary carcinoma cell line S.W. 527 is A.T.C.C. HB 8143.

EXAMPLE II

Lymphocytes are obtained from a group of patients who have been diagnosed as having auto-immune disease. These patients are pre-screened for the presence of antibodies directed against thymus derived lymphocytes (T cells). These patients are also HLA typed. The lymphocytes are processed as in Example I.

There are thus obtained cultures producing antibody with a specificity for the T lymphocyte population. In the case of blood from certain patients the specificity of hybridoma antibodies is against functionally and antigenically distinct subsets of the T cells.

A specimen of a cell line producing antibodies with the specifities for Helper-T cells has been deposited as A.T.C.C. HB 8145.

EXAMPLE III

For the production of leucocyte inhibiting factor, LIF, it is desirable, using known specific identification techniques based on the differing affinities of subsets of human T lymphocytes for sheep red blood cells, to isolate cells responsible for the production of leucocyte inhibitory factor. Thus human peripheral blood mononuclear cells are isolated on Ficoll-Hypaque gradients, washed and rosetted with sheep erythrocytes. E+cells are rosetted through Ficoll-Hypaque gradients and treated with buffered ammonium chloride to remove the red cells and washed thoroughly. E+cells are then sensitized with the monoclonal antibody Leu 3a (Bector-Dickinson), washed and rosetted (800 g for 10 minutes) with human red cells coupled with affinity column purified rabbit anti-mouse Ig. Rosetted mixture are layered onto Ficoll-Hypaque gradients and centrifuged at 100 g for 15 minutes. The Leu negative T cells remain at the interface while the Leu 3a + rosetted cells are formed in the pellet.

The Leu 3a negative cells are cultured at a concentration of $5 \times 10^6$/ml in one ml aliquots for 48 hours with the lectin known as concanavalin A (0.01 mg/ml) at 37° C. in a humid atmosphere with 5% $CO_2$. Then the supernatants of concanavalin A stimulated Leu 3a negative cells are tested for inhibitory activity to ensure LIF production. By first isolating such a LIF producing subset, the development of the human clone is greatly improved as compared to techniques using general stimulation of T cells to produce LIF. Cells from strongly positive wells are pooled and used in the fusion. The cells are washed thoroughly with commercial RPMI 1640 medium containing 10% fetal calf serum and then used as a fusion partner with a human malignant cell.

In this case, since LIF is not an antibody molecule, a malignant fusion partner of the T cell type is used, which is not capable of producing LIF. A mixture of 20,000,000 of these concanavolin A stimulated cells and 10,000,000 cells of such lymphoblast T cells, e.g. of the line designated J.M. by Rosewell Park in polyethylene glycol is centrifuged and then further treated as in Example I to effect fusion, separation, culturing and subculturing.

The following Table shows results of an assay of the potency of LIF produced by a human T cell hybridoma, (A.T.C.C. HB 8144) thus produced in 3 tests at a dilution of 1:1 to 1:1000, compared to
(a) J.M. supernatant, previously tested to ensure inactivity;
(b) Human anti-T cell hybridoma supernatant; and
(c) Positive control supernatants of freshly isolated T cells stimulated with concanavalin A for 48 hours and diluted to 1:10.

The first determinations a and b were made to minimize the possibility that the cell fusion produces a non-specific inhibitory factor.

| Potency of LIF Produced by a Human T Cell Hybridoma* | | | |
|---|---|---|---|
| | Migration Index | | |
| Clone 1B2E12 Dilution | Test 1 | Test 2 | Test 3 |
| 1:1 | 0.53 | 0.51 | 0.45 |
| 1:2 | 0.43 | 0.67 | 0.63 |
| 1:10 | 0.55 | 0.38 | 0.52 |
| 1:100 | 0.40 | 0.42 | 0.50 |
| 1:200 | 0.43 | 0.78 | 0.61 |
| 1:400 | 0.40 | 0.55 | 0.53 |
| 1:1000 | 0.64 | 0.69 | 0.71 |
| J. M. supernatant | 1.15 | 1.08 | 0.96 |
| Human anti-T cell hybridoma supernatant | 0.89 | 0.98 | 1.03 |
| Freshly produced LIF from lymphocytes stimulated with concanavalin A diluted 1:2 | 0.65 | 0.57 | 0.66 |

*Indicator cells [polymorphonuclear leucocytes (PMN)] were isolated by dextran sedimentation (molecular weight 500,000). 20% by volume of a 6% dextran solution prepared in normal saline was added to heparinized blood in a 50-ml syringe. The syringe was incubated at room temperature for 30 minutes in an upright position, and the buffy coat cells were carefully expressed. The cells were diluted in HBSS 1:2 and centrifuged through a Ficoll-diatrizoate gradient. The pelleted PMN were washed three times in HBSS, and, when necessary, any contaminating erythrocytes were lysed by hypotonic shock. The PMN were suspended in an agarose medium containing 10% horse serum and 0.1% agarose. Droplets (0.002 ml) containing cells at $10^8$/ml were dispensed with a Hamilton syringe into flat-bottomed microtitre plate wells, and 0.1 ml of hybridoma supernatant or compared supernatant was added to each of three wells. After incubation for 4-6 hours at 37° C., the areas of migration outside the droplets were calculated using an inverted microscope with a calibrated 10× ocular. The zone of migration from the edge of the droplet to the border of the migrating cells was measured in four perpendicular directions; the radius of the droplet was subtracted from the area of the migration zone. Results were expressed as a migration index calculated as area of migration in presence of mitogen divided by area of migration in absence of mitogen.

The foregoing table demonstrates that LIF has been produced in a potency several magnitudes greater than that of freshly produced LIF. Freshly produced LIF rapidly loses effectiveness on dilution and a dilution of 1:100 is practically ineffective. The foregoing preparation still shows a good effect at a dilution of 1:1000.

EXAMPLE IV

An antibody prepared in Example I is mixed with serum or ductile secretion from a woman suspected of having mammary carinoma. There is added a precipitating agent such as goat anti-human antibody, which has been radio-labeled. The mixture is centrifuged at high speed to bring down the precipitate. The precipitate is washed to remove excess radioactivity and the resulting precipitates are counted in a gamma counter.

EXAMPLE V

Lymphocytes are obtained from the blood of patients in an active stage of juvenile rheumatoid arthritis (JRA). The sera of these patients are pre-screened by an assay for binding to T cells from normal donors and their lymphocytes are HLA typed. The lymphocytes are then separated and subjected to the fusion technique as in Example I using as the malignant fusion partner lymphoblastoid T cells, e.g. the cell line from J.M. RPMI (other T or B cell lines may also be used.)

After fusion, separation, culture and subculture of the clone is conducted as in Example I. A desirable culture medium consists of 90% commercial RPMI medium plus 10% fetal bovine serum. Assays of the supernatants obtained from the subcultures and sera of the donor patients comparing reactivity to isolated T cells from normal donors prove that the clones make the same type of antibody to JRA as the patient's serum. In order to eliminate the possibility of non-specific binding caused by products resulting from the fusion process, supernatant from a human clone producing leukocyte inhibiting factor was also tested on T cells from these normal donors; a negative result was obtained.

EXAMPLE VI

Neonatal mice less than 24 hours old are injected interperitoneally with 0.03 ml of a mixture of 90% commercial RPMI 1640 culture medium and 10% fetal bovine serum, the culture medium used in Example V for subculturing. Thirty days later the mice are tested for reaction to this mixture and only the tolerized mice, which do not react, are used. These tolerized mice are injected with 0.5 ml of the supernatant mixture from the JRA clone subculture of Example V. Fourteen days later, the mice are given a booster shoot of 0.5 ml of the same supernatant.

Fourteen days later the mice are bled from the ocular sinus and the scrum is tested for anti-idiotypic antibody (antibody to hypervariable regions on the JRA autoantibody molecule). In a first test, positive mouse serum reacts with clone supernatant to cause precipitation; care should be taken to run a control with clone-free medium which should be negative.

In another available test, the anti-idiotype serum is tested with active serum from a patient in an active stage of JRA to obtain precipitation, while negative results are obtained from patients not exhibiting disease activity. Spleens from mice giving a positive test for anti-idiotype antigens are then used for fusion.

Plasmacytoma (e.g. NS-1 from the Salk Institute) is maintained in continous culture at 37° C. in $CO_2$ and used for the hybridizations. The growth medium consists of a high-glucose modified Eagle's medium (DMEM) (Gibco—Grand Island Biological, Inc., NY) with 10% fetal calf serum (FCS) and 2% antibiotic mixture containing penicillin, streptomycin, and amphotericin B. Cells are cultured in flasks or multi-well culture plates and split, with new medium added every other day. Immunoglobulin is not secreted by this line, thereby alleviating the problem of nonspecific secretion of immunoglobulin. Feeder layers of macrophage are obtained by flushing the peritoneal cavity with 5 ml 0.34M sucrose. Cells are washed in medium with 10% FCS, resuspended to $2-3\times10^4$/ml in RPMI 1640 medium and then 1 ml is added to each well of a 24-well culture plate. Incubation at 37° C. in 10% $CO_2$ is carried out for 1 hour to allow feeder cells to adhere.

Sterile spleen cells form immunotolerant or control mice are obtained by teasing in 10 ml Hank's balanced salt solution (HBSS). Cells are transferred into 15 ml centrifuge tubes, dispersed by pipetting, allowed to stand 10 minutes, transferred to 50 ml centrifuge tubes, washed twice with HBSS, resuspended and counted. Approximately $10^8$ lymphoid spleen cells are combined with $10^7$ washed myeloma cells and centrifuged at 400 g for 5 minutes. After removal of the supernatant, the cell pellet is gently resuspended and 300 ml of polyethylene glycol (PEG 4000) in HBSS with 5% DMSO are added, mixed for 30 seconds, then centrifuged at 600 rpm for 6–7 minutes at room temperature. After 8 minutes in PEG, 5 ml RPMI medium is carefully added, followed by 5 ml medium with 20% FCS. After incubation for 1 minute at room temperature, the tubes are gently swirled and then centrifuged at 1000 rpm for 5 minutes. The supernatant is removed and 5 ml HAT medium is added. After incubation at room temperature for 5 minutes the tubes are gently resuspended and the cells brought up to 48 ml in HAT medium and distributed at 1 ml in each well of 24-well cluster plates containing macrophage feeder layers. Cells are incubated at 37° C. in 10% $CO_2$. On days 1, 3, and 5 and every second day up to 2 weeks, one ml of medium is removed from the wells and replaced by fresh HAT medium up to day 14 and by RPMI 1640 plus 10% FCS medium without HAT after that.

After two weeks, viable cell populations are tested for the presence of anti-idiotypic antibody as above.

EXAMPLE VII

Human peripheral blood mononuclear cells are isolated on Ficoll-Hypaque gradients, washed and rosetted with sheep erythrocytes. E+ cells are rosetted through Ficoll-Hypaque gradients and treated with buffered ammonium chloride to remove the red cells and washed thoroughly. The T-cells thus obtained are cultured at a concentration of $2\times10^6$/ml in on ml aliquots for, 96 hours with the lectin known as phytohemaglutin (PHA) (0.01 mg/ml) at 37° C. in a humid atmosphere with 5% $CO_2$. Then the supernatants are tested for Interleukin II activity. Cells from strongly positive wells are pooled and used in the fusion. The cells are washed thoroughly with RPMI 1640 medium containing 10% fetal calf serum and then used as a fusion partner with a human malignant cell.

A mixture of 20,000,000 of these PHA stimulated cells and 10,000,000 cells of such lyphoblast T-cells, e.g., the line designated J.M. by Rosewell Park in polyethylene glycol is centrifuged and then further treated as in Example I to effect fusion, separation, culturing and subculturing.

EXAMPLE VIII

Peripheral T-cells are treated with a commercially available murine monoclonal antibody which recognizes concanavalin A inducible suppressor cells (e.g., Leu 2a Becton Dickinson). This subset of suppressor cells is then separated by indirect rosetting by the technique of Example III. The resulting subset is stimulated with concanavalin A at a concentration of 20 micrograms/ml at 37° C. for 48 hours in a humid atmosphere containing 5% carbon dioxide. After 48 hours, these stimulated cells are fused to T-cells lines which do not exhibit the presence of suppressor factors, using the methods described in Example I. Supernatants from the fusions are checked for Suppressor Factor and are tested for their ability to prevent the synthesis and/or secretion of immunoglobulin by examining the amount of immunoglobulin produced by lymphocytes stimulated by pokeweed mitogen, a known stimulator of immunoglobulin production, in the presence or absence of supernatant from putative suppressor factor fusions.

What is claimed is:

1. A human-human hybridoma designated ATCC HB-8143.

2. Monoclonal antibodies secreted by ATCC HB-8143, said monoclonal antibodies comprising IgG and IgM antibodies, both antibodies having specificity for human breast carcinoma cells.

* * * * *